US012714850B2

(12) United States Patent
Lo et al.

(10) Patent No.: US 12,714,850 B2
(45) Date of Patent: Aug. 25, 2026

(54) TRANSCUTANEOUS ELECTRICAL NERVE STIMULATION DEVICE WITH THERMAL MODALITIES FOR STIMULATING ACUPOINTS OF A USER

(71) Applicant: THE HONG KONG POLYTECHNIC UNIVERSITY, Hong Kong (CN)

(72) Inventors: Chun-Lap Samuel Lo, Hong Kong (CN); Sai Wang Seto, Hong Kong (CN); Sze Lung Kenneth Chan, Hong Kong (CN)

(73) Assignee: The Hong Kong Polytechnic University, Hong Kong (CN)

( * ) Notice: Subject to any disclaimer, the term of this patent is extended or adjusted under 35 U.S.C. 154(b) by 298 days.

(21) Appl. No.: 18/586,648

(22) Filed: Feb. 26, 2024

(65) Prior Publication Data

US 2024/0189578 A1 Jun. 13, 2024

Related U.S. Application Data

(63) Continuation-in-part of application No. PCT/CN2022/083913, filed on Mar. 30, 2022.

(51) Int. Cl.
*A61N 1/04* (2006.01)
*A61N 1/36* (2006.01)

(52) U.S. Cl.
CPC ......... *A61N 1/0456* (2013.01); *A61N 1/0476* (2013.01); *A61N 1/0484* (2013.01); *A61N 1/36025* (2013.01); *A61N 1/36034* (2017.08)

(58) Field of Classification Search
None
See application file for complete search history.

(56) References Cited

U.S. PATENT DOCUMENTS 11,633,621 B2 * 4/2023 Lim .................... A61N 5/0618 607/92
11,857,801 B2 * 1/2024 Devens ............... A61N 5/0622
(Continued)

FOREIGN PATENT DOCUMENTS

CN 105283218 B 10/2017
CN 109069828 A 12/2018
(Continued)

OTHER PUBLICATIONS

Notice of Reasons for Refusal of Japanese Patent No. 2024-553426 issued from the Japan Patent Office on Sep. 22, 2025.
Office Action of TW 112109967 issued from the Taiwan International Patent & Law Office (TIPLO) on Jul. 4, 2015.
(Continued)

*Primary Examiner* — Shirley X Jian
(74) *Attorney, Agent, or Firm* — S&F/WEHRW

(57) ABSTRACT

A head-mount transcutaneous electrical nerve stimulation (TENS) device adapted to stimulate acupoints of a user transcutaneously when being worn on the head of the user is disclosed. The TENS device includes one or more frames, a plurality of contacts, a pulse width modulation (PWM) generator, and one or more thermal pads. The one or more frames are arranged to have a contour matching an anatomical shape of the head. The plurality of contacts is arranged on an inner surface of the one or more frames for contacting the acupoints on the head. The PWM generator is configured to generate a pulse stimulation signal and couple the pulse stimulation signal to the plurality of contacts for stimulating the acupoints. The one or more thermal pads are arranged on the inner surface of the one or more frames for applying thermal treatment to the acupoints.

24 Claims, 9 Drawing Sheets

(56) References Cited

U.S. PATENT DOCUMENTS

2006/0052834 A1* 3/2006 Goroszeniuk ...... A61N 1/36021 607/46
2008/0027509 A1 1/2008 Andino et al.
2010/0125190 A1* 5/2010 Fadem .................. A61B 5/377 600/383
2012/0016446 A1 1/2012 Panting
2013/0085317 A1 4/2013 Feinstein
2014/0070957 A1* 3/2014 Longinotti-Buitoni ...................... G06F 1/163 340/870.01
2015/0257674 A1* 9/2015 Jordan ................. A61B 5/0006 600/383
2017/0136235 A1* 5/2017 Molsberger .......... A61N 1/0492
2017/0165485 A1* 6/2017 Sullivan ............... A61B 5/0022
2018/0345006 A1* 12/2018 Ambrose ............. A61B 5/0536
2019/0021665 A1* 1/2019 Kesinger .............. A61B 5/6803
2020/0238097 A1* 7/2020 Connor ................ A61N 5/0622
2020/0246616 A1 8/2020 Simon et al.
2020/0306536 A1* 10/2020 Wang ....................... A61H 1/00
2021/0015393 A1* 1/2021 Jordan .................. A61B 5/291
2022/0054856 A1* 2/2022 Wang .................. A61N 5/0618
2023/0110636 A1* 4/2023 Wang .................. A61N 1/0484 607/3

FOREIGN PATENT DOCUMENTS

CN 109199670 A 1/2019
CN 112206416 A 1/2021
CN 112601488 A 4/2021
CN 113101518 A 7/2021
CN 113631219 A 11/2021
JP S6428657 U 2/1989

OTHER PUBLICATIONS

Office Action of TW 112109967 issued from the Taiwan International Patent & Law Office (TIPLO) on Feb. 19, 2015.
Office Action of TW 112109968 issued from the Taiwan International Patent & Law Office (TIPLO) on Jan. 10, 2015.
Extended European Search Report; PCT Application No. Application PCT/CN2022083913 Issued from the European Patent Office on Sep. 2, 2025.

* cited by examiner

300 { 310, 320, 330

TRANSCUTANEOUS ELECTRICAL NERVE STIMULATION DEVICE WITH THERMAL MODALITIES FOR STIMULATING ACUPOINTS OF A USER

CROSS-REFERENCE TO RELATED APPLICATIONS

This application is a bypass continuation of International Application Number PCT/CN2022/083913, filed Mar. 30, 2022, entitled "TRANSCUTANEOUS ELECTRICAL NERVE STIMULATION DEVICE WITH THERMAL MODALITIES FOR STIMULATING ACUPOINTS OF A PATIENT WITH DEMENTIA", hereby incorporated herein by reference as to its entirety.

FIELD OF THE INVENTION

The present disclosure generally relates to a device and a method for improving cognitive functions in users, such as dementia patients. In particular, the present disclosure relates to an ultra-low constant current head-mount transcutaneous electrical nerve stimulation (TENS) device with thermal modalities adapted to stimulate acupoints to improve cognitive functions in dementia patients.

BACKGROUND OF THE INVENTION

Neurodegenerative disease, also sometimes referred to as Alzheimer's disease and Parkinson's disease, is an umbrella term for a range of diseases affecting the nerve cells in the human brain or the peripheral nervous system. This is generally an age-dependent disease, which becomes increasingly prevalent due to the rising elderly population in the community. The patients with the neurodegenerative disease suffer progressive deterioration of brain function, which cause dementia with symptom associated with mobility, coordination, strength, speech, memory, cognition, swallowing ability, etc. There is no effective therapeutics to cure neurodegenerative diseases, and the treatments may only help to relieve some of the physical or mental symptoms related.

Another group of patients suffers from dementia known as vascular dementia. It is mostly due to problems associated with poor blood circulation to the brain. Pre-disposed medical problems including high blood pressure, smoking, diabetes, high cholesterol, history of mild warning strokes, evidence of disease in arteries elsewhere and heart rhythm abnormalities may contribute to vascular dementia. Pure vascular dementia is relatively rare, which statistically contributes to approximately 10% of cases only. Most of the patients suffer from a mixture of dementia due to various types of neurodegenerative diseases in combination with vascular dementia.

There are both drugs and non-drug treatments that can lessen the symptoms of the patients. Non-drug interventions aim to procrastinate mental abilities degeneration and help the patients to stay more independent in daily life, and to improve their wellbeing and quality of life.

There are pieces of evidence showing that glucose or energy deprivation in the brain may be the first step towards Alzheimer's disease. By improving the blood circulation in patients with vascular dementia, neurons are provided with the nutrients and energy for supporting their metabolism and regenerative needs. To this end, TENS was suggested to be useful. TENS is a therapeutic procedure involving the use of electric current to stimulate peripheral nerves underneath the skin. It is believed that TENS, being non-invasive and having relatively minimum side effects, can be a treatment option for dementia patients by improving the blood circulation to the brain. Evidence from recent research with animals and humans supports the effectiveness of the use of TENS for improving cognitive functions.

Hippocampus and Cholinergic basal forebrain (CBF) system plays an important role in memory processes [1], [2]. Results of neurophysiological studies on animals demonstrated that TENS could stimulate the CBF system via different pathways in order to improve the memory and cognitive functions. In animal studies with rats, TENS could stimulate the hippocampus directly via spinoseptal pathway [3], [4], and stimulate CBF system indirectly via brain nuclei [5], [6], [7]. In neuroanatomical studies with rats, 2 brain nuclei, namely locus coeruleus (LC) and dorsal raphe nucleus (DRN), are identified as major sources of the noradrenergic and serotonergic neurotransmitter systems respectively [8], [9]. Both LC and DRN provide anatomical substrates, which relay the TENS signal and stimulate the CBF system through rostral projections of noradrenergic and serotonergic neurotransmitter systems [5], [6], [7]. In addition, a recent review concluded that TENS, a kind of neuronal stimulation, could induce neuronal reactivation of metabolically impaired neurons [10], which could explain the improved cognitive functions following repetitive TENS. In human studies, TENS has been found to improve memory and cognitive functions in people having cognitive disorders (e.g.: Alzheimer's disease) and non-demented older adults. In a series of studies on patients having different stages of Alzheimer's disease [11], [12], [13], repetitive TENS (5 days a week for 6 weeks) could induce significantly greater improvement in non-verbal short-term and long-term memory, verbal long-term memory, and word fluency when compared with those receiving placebo stimulation. In another clinical trial [14], TENS induced greater beneficial effects on short-term and long-term memory in patients at an early stage of Alzheimer's disease, when compared with those at mid-stage of Alzheimer's disease. In contrast, a recent study demonstrated that TENS did not show any positive effect on various aspects of memory in patients with the pre-clinical stage of dementia (i.e., older adults with mild cognitive impairments) [15]. A review of 8 studies on the effects of TENS on non-pain related cognitive and behavioral functioning in patients with Alzheimer's disease and non-demented patients concluded that TENS could improve memory, affective behavior, and rest-activity rhythm in patients having Alzheimer's disease [16].

In traditional Chinese medicine, the practice of acupuncture has a long history that can be used to achieve special and designated therapeutic effects. Acupuncture involves the insertion of thin needles very accurately through the skin at the acupoints, which must be performed by a professional acupuncturist. The advantages and therapeutic effects of acupuncture to patients suffering from vascular dementia are constantly discussed and acknowledged, but such alternative medicine is less popular and generally less accessible by the elderly community.

The concept of the use of a combination of TENS and acupuncture is also proposed. This is considered to be better than pure acupuncture as there is no skin puncture and very accurate localizing of the acupoints is not required. TENS is different from transcranial magnetic stimulation (TMS) and transcranial different current stimulation (tDCS) in which both the latter do not observe the need to use acupuncture points. Electroacupuncture was also exploited for ameliorating vascular dementia symptoms [17], which effectively improved the cognitive function of patients with mild cognitive impairment.

Commercially, handheld TENS devices have been developed and commercialized to deliver a concentrated microcurrent for pain management, muscle stimulation, stroke rehabilitation, and cardiovascular disease treatment [18], [19]. Since it was first patented in 1991 under the U.S. Pat. No. 4,989,605A, numerous companies have also developed different devices for pain therapy. Some devices are designed with a controller having 4 to 8 pads for providing various massage modes for domestic use. The user may place the device at desired positions for pain relief and comfort. The frequency of the currents from such devices is usually between approximately 10 Hz and 50 Hz and the current administrated is in the mini-Ampere (mA) range. One of the most perceived dangers was the strength of the current being delivered and used. As said, TENS devices available commercially deliver TENS currents in the mA range and that is too strong to bear for most people, not to mention the potential of causing burns and feeling of sharp pain. Furthermore, it is difficult for untrained caregivers to use the TENS devices for stimulating particular acupoints for improving the cognitive functions and memory of vascular dementia patients.

Accordingly, there is a need in the art to have a head-mount device that can be used easily by untrained caregivers for stimulating selected acupoints for improving the cognitive functions and memory of dementia patients. Furthermore, other desirable features and characteristics will become apparent from the subsequent detailed description and the appended claims, taken in conjunction with the accompanying drawings and this background of the disclosure.

SUMMARY OF THE INVENTION

Provided herein is an ultra-low constant current head-mount TENS device with thermal modalities adapted to stimulate acupoints. It is the objective of the present disclosure to provide stimulation to selected acupoints on the head of a patient for treating or preventing dementia, thereby the cognitive functions of the dementia patient are improved.

In one or more embodiments there is provided a head-mount TENS device is adapted to stimulate acupoints of a user transcutaneously when being worn on the head of the user. The TENS device includes one or more frames, a plurality of contacts, a pulse width modulation (PWM) generator, and one or more thermal pads. The one or more frames are arranged to have a contour matching an anatomical shape of the head. The plurality of contacts is arranged on an inner surface of the one or more frames for contacting the acupoints on the head. The PWM generator is configured to generate a pulse stimulation signal and couple the pulse stimulation signal to the plurality of contacts for stimulating the acupoints. The one or more thermal pads are arranged on the inner surface of the one or more frames for applying thermal treatment to at least one of the acupoints.

In an embodiment, the plurality of contacts includes a first group of contacts configured for contacting Baihui (GV-20) and Sishencong (EX-HN1) acupoints of the user; a second group of contacts configured for contacting Fengchi (GB-20) acupoints of the user; and a third contact configured for contacting Shenting (GV-24) acupoint of the user.

In an embodiment, the first group of contacts includes a first contact pad positioned for contacting the Baihui (GV-20) acupoints, and four adjacent contact pads positioned around the first contact pad for contacting the Sishencong (EX-HN1) acupoints.

In an embodiment, each individual contact of the plurality of contacts has a resilient structure made of a low resistance conductive material.

In one embodiment, the individual contact includes a spring and a contact pad, wherein the spring is arranged to press the contact pad against the head at the acupoints. Optionally, the contact pad is a circular plate electrically connected to the PWM generator for coupling the pulse stimulation signal or to a low reference voltage. Alternatively, the contact pad comprises a first zone and a second zone. The first zone and the second zone are separated by an insulating material, and the first zone is electrically connected to the PWM generator for coupling the pulse stimulation signal and the second zone is electrically connected to the low reference voltage.

In another embodiment, the individual contact includes a spring and a contact pad having plural pin electrodes, wherein the spring is arranged to press the plural pin electrodes through the hair of the user against the head at the acupoints. Optionally, at least one pin electrode of the plural pin electrodes is electrically connected to the PWM generator for coupling the pulse stimulation signal, and at least one other pin electrode of the plural pin electrodes is electrically connected to a low reference voltage.

In an embodiment, the pulse stimulation signal has an ultra-low current of not more than 20 μA, and preferably the ultra-low current is between 1 μA and 8 μA. Optionally, the pulse stimulation signal is a square wave with a pulse frequency of 50 Hz to 200 Hz, and preferably the pulse frequency is between 96 Hz and 100 Hz.

In an embodiment, the one or more thermal pads are configured to deliver heat to at least one of the acupoints of the user and areas proximate to the at least one of the acupoints.

In an embodiment, each of the one or more thermal pads includes a winding of a thermally conductive material for delivering thermal energy to at least one of the acupoints and the areas proximate to the at least one of the acupoints with a temperature ranging between 36° C. and 40° C.

In an embodiment, the one or more frames includes an upper frame at least partially covering a frontal region and a parietal region of the head, and a lower frame at least partially covering an occipital region of the head.

In an embodiment, the upper frame and the lower frame are adjustably connected together using connection means. Optionally, the connection means includes straps or belts for providing a flexibility to adjust the contour for matching the anatomical shape of the head.

In an embodiment, the head-mount TENS device includes fastening means for applying a tension on the upper frame and the lower frame toward the acupoints. Optionally, the fastening means includes a chin strap fastened around the user's chin and two transverse straps extending from the upper frame to the lower frame, wherein the chin strap and each of the transverse straps are connected to form a Y-shaped configuration around an otic region for securing the head-mount TENS device in position on the head.

In an embodiment, the head-mount TENS device includes one or more temperature sensors for obtaining temperature readings of areas proximate to the one or more thermal pads; a current sensor for detecting an electric current flowing through the user via the plurality of contacts; and a processor configured to monitor and adjust the one or more thermal pads and the PWM generator continuously based on the temperature detected by the one or more temperature sensors and the electric current detected by the current sensor.

In one or more embodiments there is provided a TENS device adapted to stimulate acupoints of a user transcutaneously. The TENS device includes a head article; a plurality of contacts hidden within the head article for contacting the acupoints on the head; a PWM generator configured to generate a pulse stimulation signal and couple the pulse stimulation signal to the plurality of contacts for stimulating the acupoints; and one or more thermal pads hidden within the head article for applying thermal treatment to the acupoints.

In an embodiment, TENS device includes fastening means for applying a tension to hold the TENS device tightly on the head.

In an embodiment, the head article is a helmet, a hat, a headband, a crown, a headgear, a headwear, a hood, or any combination thereof.

In one or more embodiments there is provided a method of stimulating selected acupoints in a user, including the steps of positioning a TENS device on the head of the user, wherein the TENS device comprises a plurality of contacts and one or more thermal pads arranged on an inner surface for contacting acupoints on the head; generating, by a PWM generator, a pulse stimulation signal; coupling the pulse stimulation signal to the plurality of contacts for stimulating the acupoints transcutaneously; and enabling the one or more thermal pads for applying thermal treatment to the acupoints.

In an embodiment, the method includes the steps of recording an electric current flowing through the user and temperature readings of areas proximate to the one or more thermal pads; storing the electric current and the temperature readings locally in a memory of the TENS device; and uploading the electric current and the temperature readings to a cloud system for medical practitioners or therapists to access.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which:

FIG. 1A, FIG. 1B, and FIG. 1C, illustrate the locations of acupoints Baihui (GV-20), Sishencong (EX-HN1), Fengchi (GB-20), and Shenting (GV-24), in which these identified acupoints may provide beneficial effects to a dementia patient when appropriately stimulated;

DETAILED DESCRIPTION OF THE INVENTION

Figures 1A, 1B, 1C:
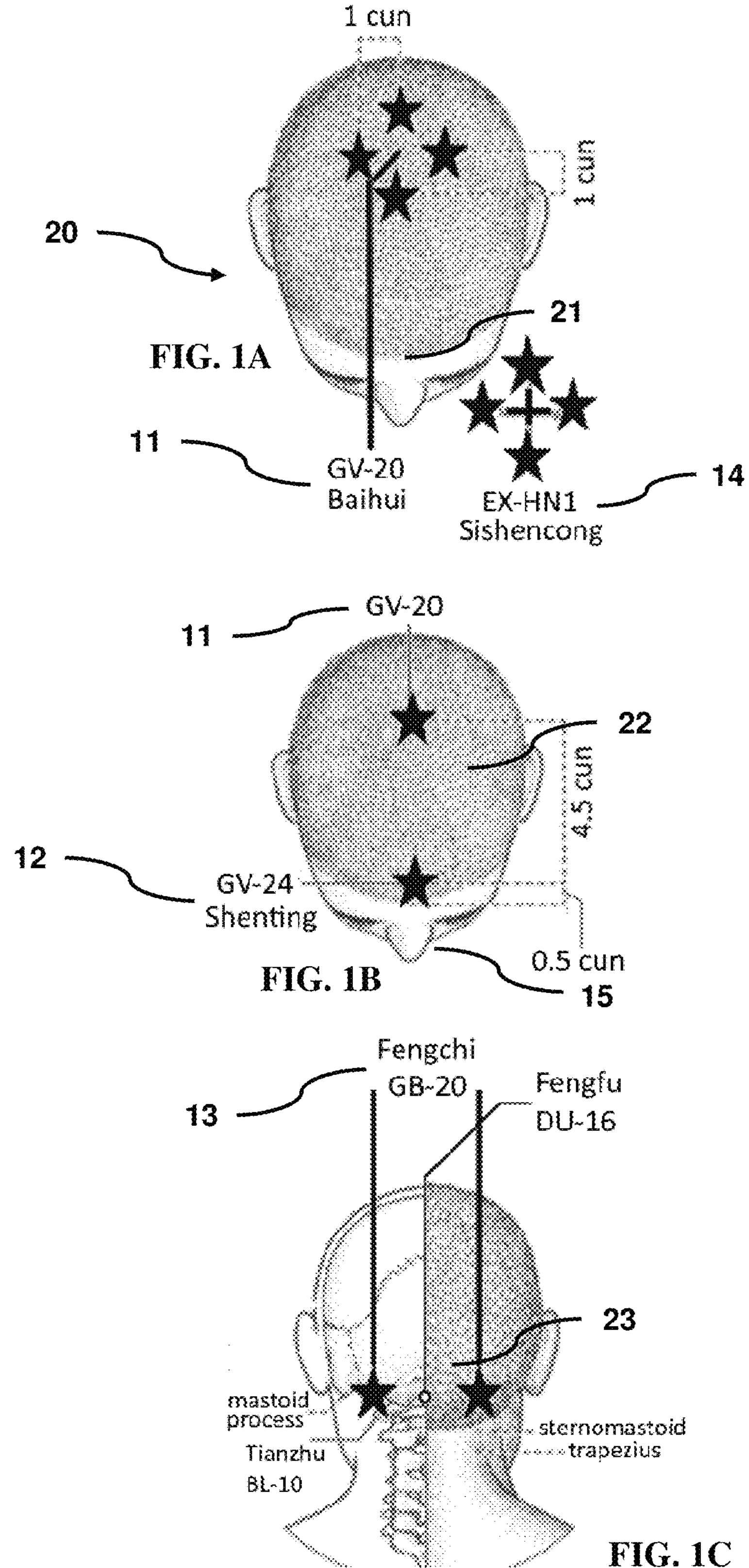
FIGS. 1A-1C, comprising

The present disclosure generally relates to a device and a method for improving cognitive functions in users. A user may be a dementia patient or an individual that suffers from other cognitive impairments and therefore needs treatment. A user may alternatively be a human with no cognitive impairments and this human's cognitive condition can be preferably improved or bettered with the assistance of the device or method as described herein with reference to one or more embodiments. More specifically, but without limitation, the present disclosure provides an ultra-low constant current head-mount transcutaneous electrical nerve stimulation (TENS) device with thermal modalities. One or more embodiments of the present disclosure provide stimulation to selected acupoints on the head of a patient for treating or preventing dementia, thereby the cognitive functions of the dementia patient are improved.

The present disclosure provides a safe and reliable means for treating and improving the condition known as dementia. As discussed in the previous sections, dementia is caused by neurodegenerative diseases, such as Alzheimer's disease and Parkinson's disease. The use of TENS is a proven therapy for providing beneficial effects to patients, which can provide both long-term and short-term improvements on cognitive behavior. This device of the present disclosure is designed for the convenience of the caregiver and the patient. Most importantly, the device is non-invasive, and the use is essentially painless. The caregiver can conveniently put the device on the head of the patient and the device remains in place as the patient is capable of doing other tasks or simple exercises. It should also be stressed that provision of the laymen-administrator-orientated device alleviates the constant need of physiotherapists and traditional Chinese acupuncture practitioners for administration of the treatment. Further, with the device, various selected acupoints may be electrically stimulated transcutaneously with slight warmth treatment for enhancing blood circulation. Additionally, the data collected can be streamed back using wireless communication for caregivers, medical practitioners, or therapists to gauge the treatment conditions of the patient.

The benefits, advantages, solutions to problems and any element(s) that may cause any benefit, advantage, or solution to occur or become more pronounced are not to be construed as critical, required, or essential features or elements of any or all of the claims. The invention is defined solely by the appended claims including any amendments made during the pendency of this application and all equivalents of those claims as issued.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention. As used herein, the term "proximate" when used in relation to a position refers to an area within +/−1 centimeters of the position, and preferably within +/−0.5 centimeters of the position.

As used herein and in the claims, "couple" or "connect" refers to electrical coupling or connection either directly or indirectly via one or more electrical means unless otherwise stated. The recitation of ranges of values herein is not intended to be limiting, but rather relates individually to any and all values falling within the range, unless otherwise indicated herein.

The present disclosure is based on the doctrine of acupuncture, which is an alternative medicine that treats patients by insertion and manipulation of needles in the body at selected locations. As used herein and in the claims, the acupoints, or sometimes referred to as "acupuncture points", are those selected locations in the human body. Generally, the acupoints are identified by a name followed by a reference formed by a combination of letters and a number. From the reference, the body organ or tissue location associated with, or affected by, that acupoint can be identified.

As used herein and in the claims, "transcutaneous electrical nerve stimulation" or "TENS" may refer to the therapeutic procedure involving the use of electric current to stimulate peripheral nerves underneath the skin. If the location of stimulation is selected in accordance with the traditional acupuncture therapy, the therapy may be referred to as electroacupuncture. Traditional acupuncture requires the insertion of thin needles very accurately through the skin at the acupoints. The TENS device of the present disclosure is not using such thin needles, but some electrodes or contact pads arranged to be placed on the skin for stimulation.

Referring to FIGS. 1A-1C, the locations of acupoints Baihui (GV-20) 11, Sishencong (EX-HN1) 14, Fengchi (GB-20) 13, and Shenting (GV-24) 12 are shown, which are the selected acupoints in accordance with the present disclosure. In the literature, the therapeutic effects of simulating different acupoints have been widely studied using different cognitive tests. Most previous studies concluded that TENS treatment on vascular dementia patients is effective, although sometimes the effect is temporary.

The present disclosure provides a selection of acupoints that potentially can be used for treating vascular dementia. Based on the studies of the modern literature, Baihui (GV-20) 11, Sishencog (EX-HN1) 14, Fengchi (GB-20) 13, Shuigou (GV-26) 15, and Shenting (GV-24) 12 appear to be the most relevant acupoints that are potentially capable of providing stimulation to the dementia patients as a treatment of vascular dementia.

In the practice of Chinese medicine, the acupoints may provide beneficial effects to the patient when appropriately stimulated. The use of TENS on selected acupoints can achieve even better designated therapeutic effects. As there is no skin puncture, the operation can be performed by the caregivers without the need of a professional acupuncturist. However, the accuracy in contacting and stimulating the acupoints should not be sacrificed. Among the above listed relevant acupoints, Baihui (GV-20) 11, Sishencog (EX-HN1) 14, Fengchi (GB-20) 13, and Shenting (GV-24) 12 on the head 20 are selected to be stimulated using the TENS device of the present disclosure. These acupoints are selected with the consideration of the case of developing a device that can accurately fit TENS electrodes and thermal pads thereon. As shown in FIGS. 1A-1C, all these selected acupoints are positioned on the head 20. In particular, the Baihui (GV-20) 11 and the Sishencog (EX-HN1) 14 are at the parietal region 22. The Sishencog (EX-HN1) 14 are positioned around the Baihui (GV-20) 11 with 1 cun apart. The Shenting (GV-24) 12 is located at the frontal region 21, which is 0.5 cun above the midpoint of the anterior hairline. The Fengchi (GB-20) 13 is located at the occipital region 23, which is the meeting place of the base of the skull and the top of the neck.

Figure 2:
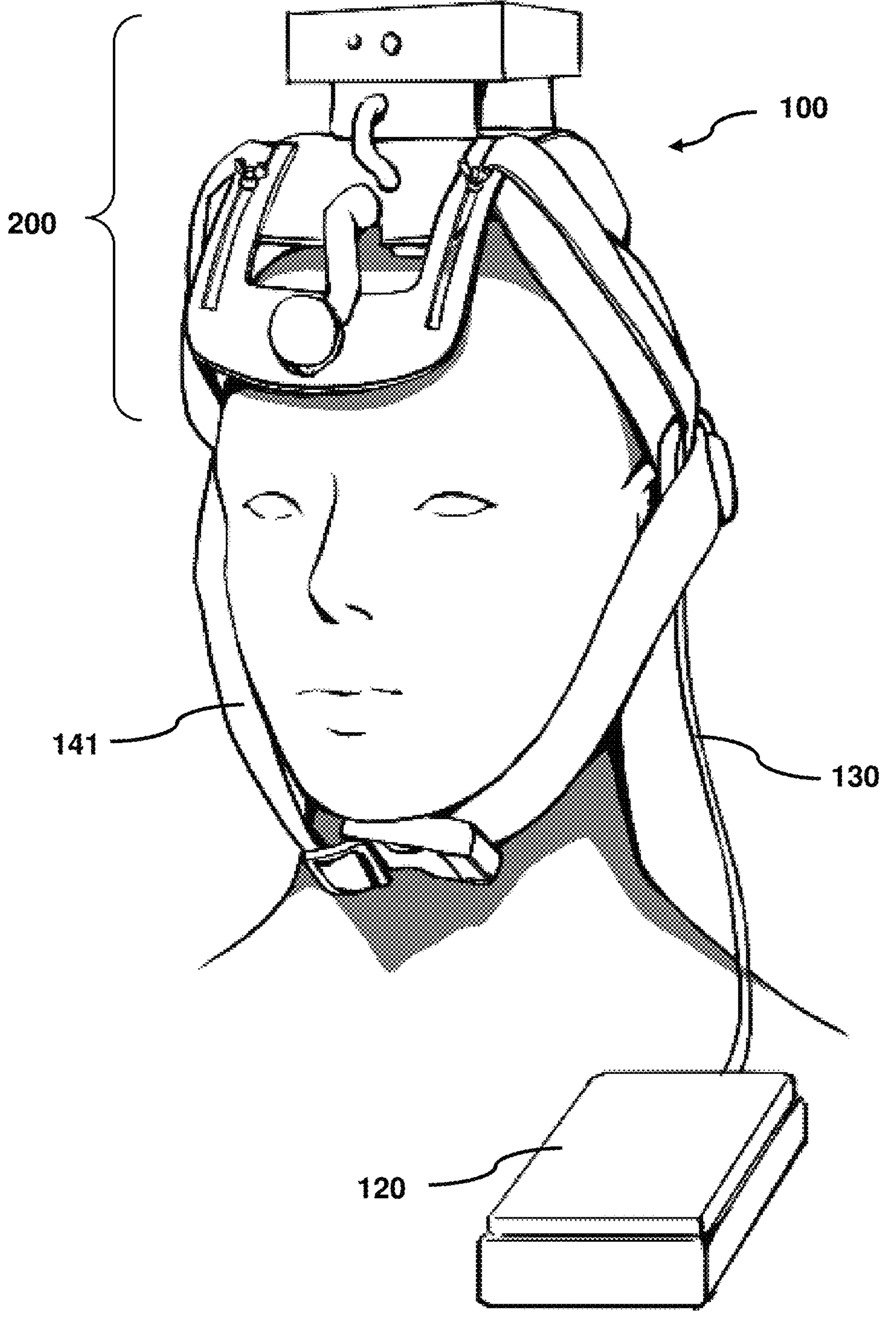
FIG. 2 illustrates a patient wearing an exemplary head-mount TENS device in accordance with certain embodiments of the present disclosure.
Figure 3:
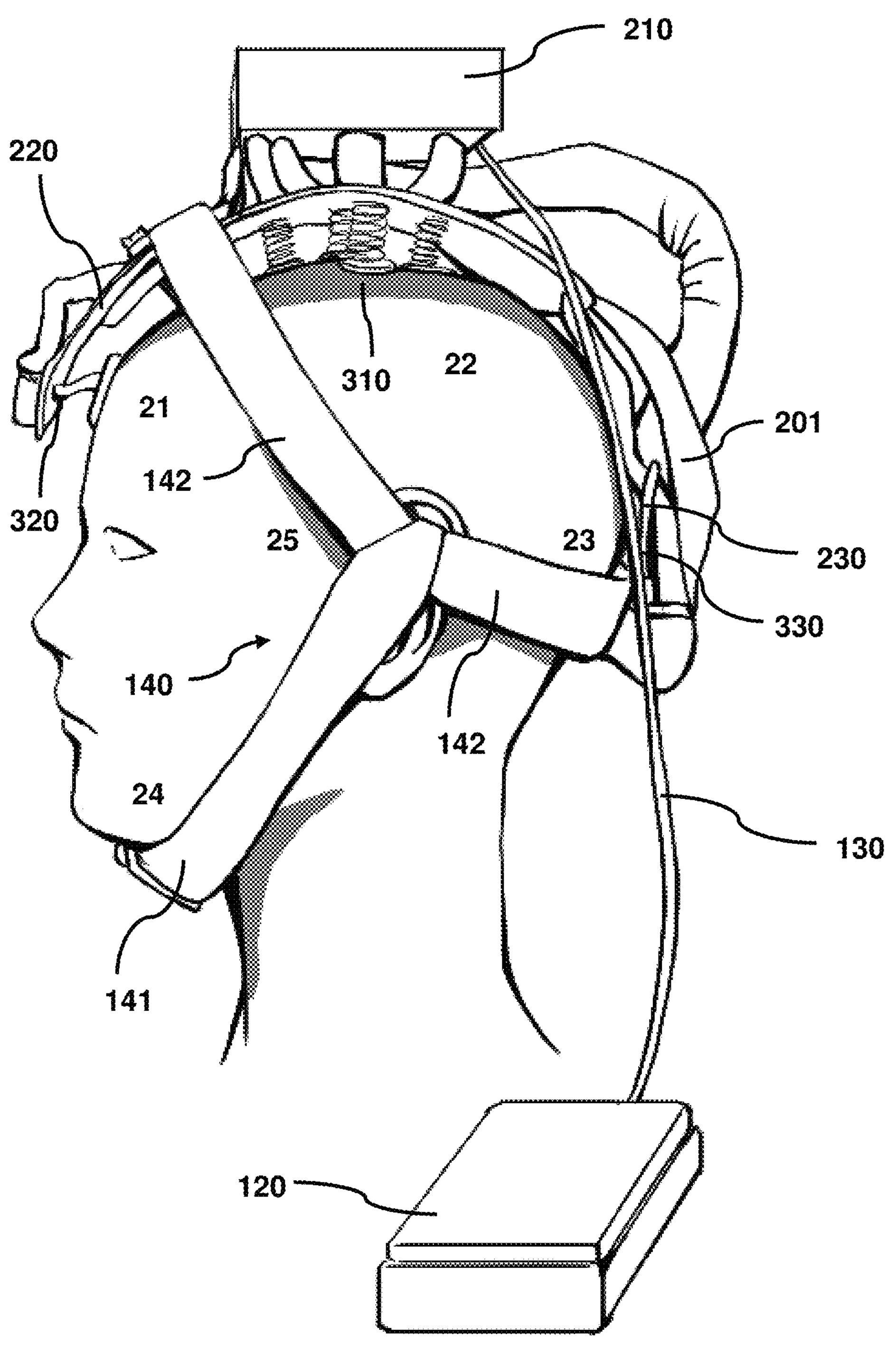
FIG. 3 is a side view of FIG. 2.
Figure 4:
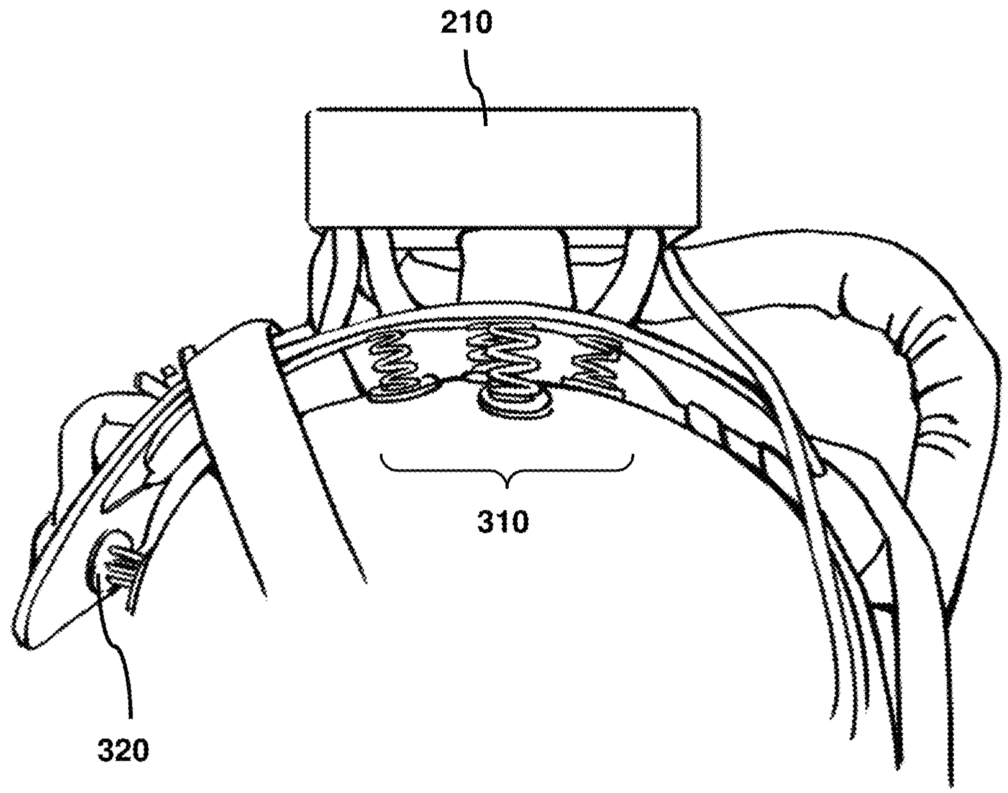
FIG. 4 is an enlarged view of FIG. 3 showing that the exemplary head-mount TENS device has a shape conformed with the skull of a normal adult.

Various views of a non-limiting exemplary head-mount TENS device 100 are shown in FIGS. 2-4. The head-mount TENS device 100 is adapted to stimulate acupoints of a patient transcutaneously for treating or preventing dementia when being worn on the head 20 of the patient. By putting the TENS device 100 on the head 20 properly, the TENS electrodes are placed accurately on top of the selected acupoints without any professional help. Therefore, it is possible for a normal caregiver to use the TENS device 100 to provide stimulation on the acupoints to improve the cognitive functions of dementia patients. In one preferred therapy, the dementia patient wears the TENS device 100 for at least 1 hour per day while capable of doing other tasks, and data collected would keep logs for caregivers, medical practitioners, or therapists to gauge the treatment conditions.

The TENS device 100 may comprise a head article with a plurality of contacts 300 and one or more thermal pads hidden within for providing stimulation to the head 20 of the patient. It is appreciated that the head article may have different shapes and configurations. For example, the head article may be a helmet, a hat, a headband, a crown, a headgear, a headwear, a hood, or any combination thereof. In certain embodiments, the head article may also include fastening means for applying a tension to hold the TENS device tightly on the head 20 of the patient such that the acupoints can be stimulated. The illustrated embodiment is a non-limiting example of the TENS device 100, which is sometimes referred to as a "head-mount TENS device" in the claims and the description. The TENS device 100 is formed by one or more frames 200 arranged to have a contour matching an anatomical shape of the head 20. Preferably and optionally, the one or more frames 200 include an upper frame 220 and a lower frame 230, which are adjustably connected together using connection means 201. The upper frame 220 and the lower frame 230 may include insert slots 145 (shown in FIG. 5) or other mounting holes for the connection means 201 and the fastening means 140 (to be discussed in details below) to provide fixation. Preferably, the connection means 201 may include straps or belts that can be adjusted in length for providing a flexibility to adjust the contour for matching the anatomical shape of the head 20, thereby the TENS device 100 can fit for patients of different head sizes. The upper frame 220 is at least partially covering the frontal region 21 and the parietal region 22 of the head 20 for stimulating the Baihui (GV-20) 11, Sishencog (EX-HN1) 14, and Shenting (GV-24) 12 on the head 20. The lower frame 230 is at least partially covering the occipital region 23 of the head 20 for stimulating the Fengchi (GB-20) 13 on the head 20.

The TENS device 100 further includes fastening means 140 for applying a tension on the upper frame 220 and the lower frame 230 toward the acupoints. The function of the fastening means 140 is to ensure that the TENS device 100 can be fitted on the head 20 of the patient and would not fall off when the patient is doing other tasks or even exercises.

Whilst a range of different fastening means 140 are contemplated, in the illustrated embodiment, the TENS device 100 is fastened to the head 20 of the patient by the fastening means comprising a chin strap 141 and two transverse straps 142. The chin strap 141 is fastened around the patient's chin 24. The transverse strap 142 is extended from the upper frame 220 to the lower frame 230. There is one transverse strap 142 on the left side of the upper frame 220, and another transverse strap 142 on the right side of the upper frame 220. It is apparent that the two transverse straps 142 may alternatively be replaced by one longer transverse strap arranged from one side of the upper frame 220, across the lower frame 230 to the second side of the upper frame 220. The chin strap 141 and each of the transverse straps 142 are connected to form a Y-shaped configuration around an otic region 25 of the head 20 for securing the TENS device 100 in position on the head. In certain embodiments, the chin strap 141 and the two transverse straps 142 may also include velcro tapes, buttons, or other fasteners for improving the compatibility of the TENS device 100 on different patients with different head shapes.

On the inner surface of the one or more frames 200, there is provided a plurality of contacts 300 for contacting the acupoints on the head 20, and one or more thermal pads 340 (refer to FIG. 5) for applying thermal treatment to the acupoints. The plurality of contacts 300 is arranged in groups. In the preferred embodiment, the plurality of contacts 300 comprises three groups of contacts. The first group of contacts 310 is configured for contacting Baihui (GV-20) 11 and Sishencong (EX-HN1) 14 acupoints of the patient. The second group 330 of contacts configured for contacting Fengchi (GB-20) 13 acupoints of the patient. The third contact 320 is configured for contacting Shenting (GV-24) 12 acupoint of the patient. The inventor has found that the improvement in the cognitive functions of patients with dementia is most significant when all three groups of contacts are utilized for stimulating the patient. However, it is apparent that the stimulation may be performed on any one or two groups of contacts without departing from the scope and spirit of the present disclosure. In the cases of having any one or two groups of contacts, the TENS device 100 can still achieve a reasonable improvement in the cognitive functions to the patient.

A control box 210 is attached to the upper frame 141, and preferably placed on top of the upper frame 141. The control box 210 includes an electric circuit board and associated accessories for controlling the plurality of contacts 300 and the one or more thermal pads 340. Electric wirings are provided to connect the control box 210 to the upper frame 220 and the lower frame 230. In certain embodiments, the control box 210 can be connected to a battery 120 via a cable 130. In an alternative embodiment, the battery 120 may be located within the control box 210. The control box 210 further comprises a communication module for transmitting and receiving signals from a portable device or a computer device using Bluetooth or other wireless communication protocols.

The TENS device 100 further comprises a pulse width modulation (PWM) generator 740 (shown in FIG. 7) configured to generate a pulse stimulation signal and couple the pulse stimulation signal to the plurality of contacts 300 for stimulating the acupoints. In certain embodiments, the PWM generator 740 is positioned within the control box 210. In previous studies, usually the TENS currents of 0.7 mA or higher, and constant voltages were used. These TENS devices, currently available commercially, are too strong to bear by most people. In some cases, continuous use of the TENS device may cause burn and sharp pain to the patient. This is caused by the mA range of TENS currents, which usually elicits a strong pulse with a stressful and painful sensation on the patient. In the present disclosure, the TENS device 100 uses an ultra-low constant current for a longer period of time of over 60 minutes to minimize the painful sensation on the patient. Particularly, the pulse stimulation signal has an ultra-low current of not more than 20 μA, and preferably the ultra-low current is between 1 μA and 8 μA. In certain embodiments, the pulse stimulation signal is a square wave with a pulse frequency of 50 Hz to 200 Hz, and more preferably the pulse frequency is between 96 Hz and 100 Hz. The current is constant, and the pulse width is less than 120 ms. The ultra-low current is delivered to each of the acupoints for stimulation by coupling the pulse stimulation signal and a low reference voltage to the patient. Preferably, the low reference voltage has a ground (GND) voltage potential.

Figure 5:
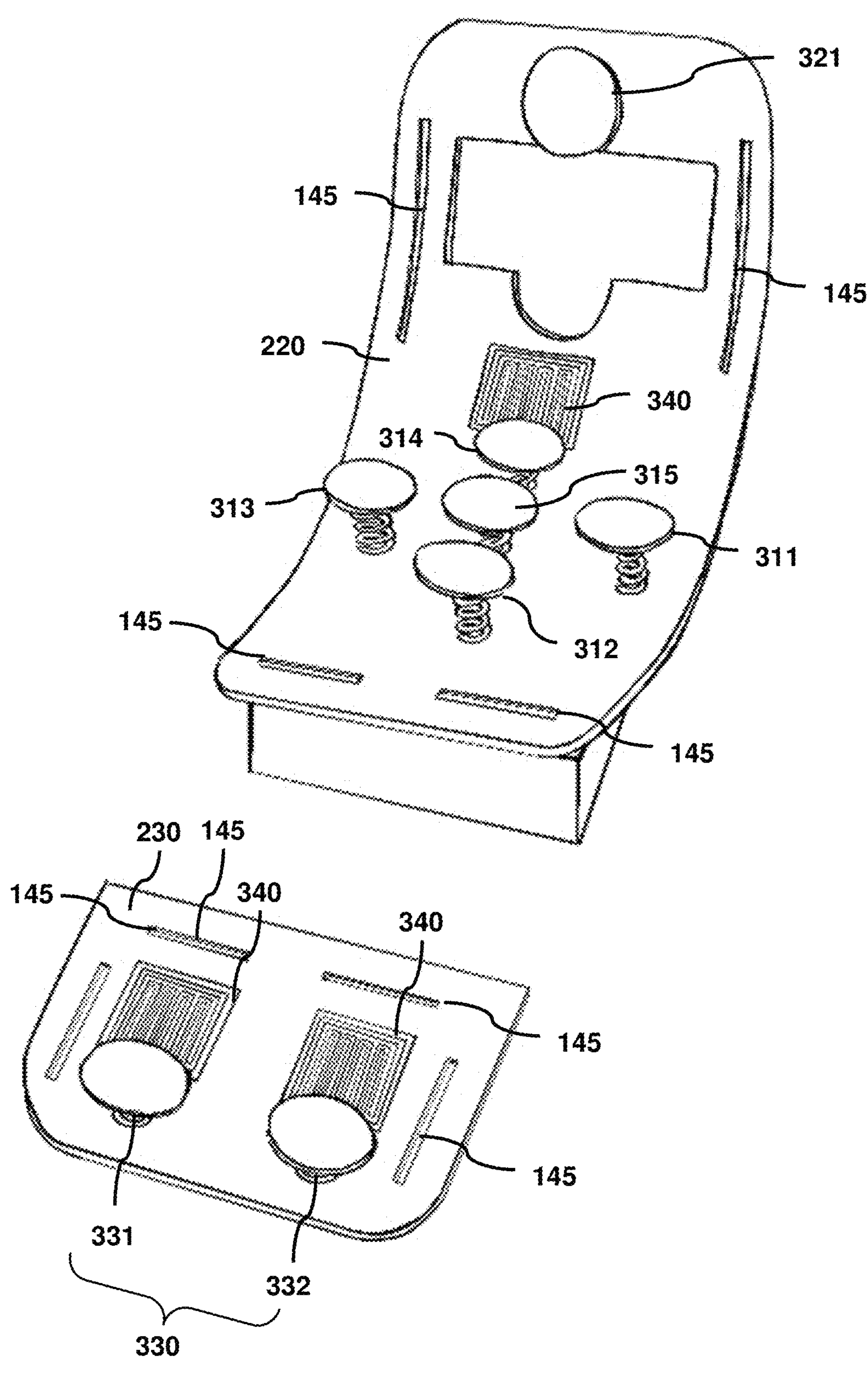
FIG. 5 illustrates an inner surface of the exemplary head-mount TENS device in accordance with certain embodiments of the present disclosure.

FIG. 5 illustrates an inner surface of the TENS device 100 in accordance with the present disclosure. The three groups of contacts 310, 320, 330 are shown. The first group of contacts 310 comprises a first contact pad 315 positioned for contacting the Baihui (GV-20) 11 acupoints, and four adjacent contact pads 311, 312, 313, 314 positioned around the first contact pad 315 for contacting the Sishencong (EX-HN1) 14 acupoints. The second group of contacts 330 is provided on the lower frame 230 so that the second and third contact pads 331, 332 can be adjustably placed on the occipital region 23 of the head 20. The caregiver can first identify the base of the skull and the top of the neck, then adjust the connection means 201 for placing the second and third contact pads 331, 332 about the Fengchi (GB-20) 13 acupoints. The third group of contacts 320 comprises a fourth contact pad 321 provided on the front part of the upper frame 220, which is positioned for contacting the Shenting (GV-24) 12 acupoint.

Figure 6:
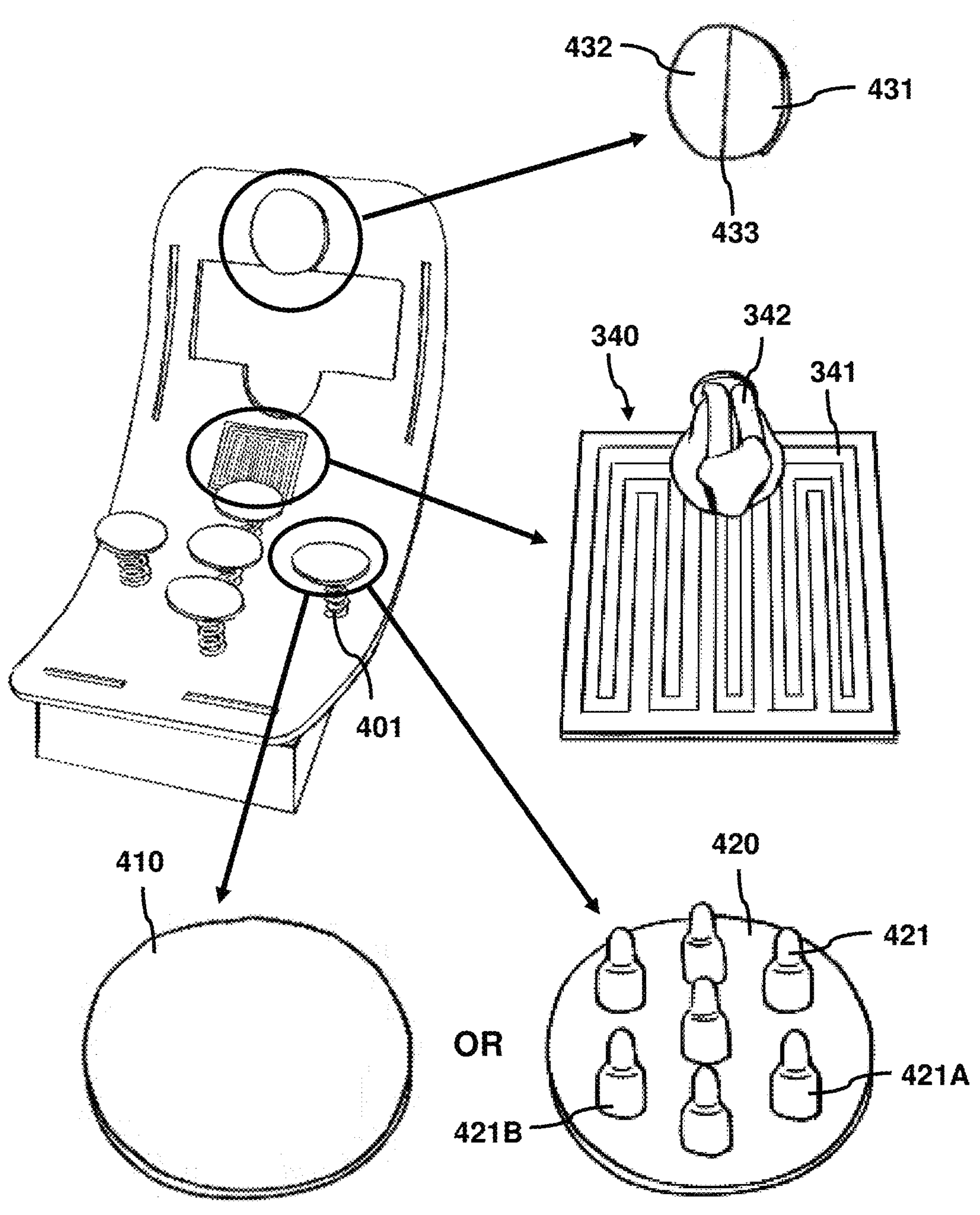
FIG. 6 illustrates three possible embodiments of the contact pads and the heating pads in accordance with certain embodiments of the present disclosure.

The shape of the head 20 differs depending on each patient, therefore it is essential for the plurality of contact pads 300 to have a resilient structure. FIG. 6 shows three possible embodiments of the contact pads which provide different advantages.

In the first embodiment, each individual contact of the plurality of contacts 300 comprises a spring 401 and a contact pad 410. The spring 401 is arranged to press the contact pad 410 against the head 20 at the acupoints. Preferably, the contact pad 410 is a circular plate. Alternatively, the spring 401 and the contact pad 410 may be replaced by a resilient member or a piston without departing from the scope and spirit of the present disclosure. The first embodiment is developed for patients with less hair, and is preferably used in the first group of contacts 310, with the first contact pad 315 as the negative terminal, and four adjacent contact pads 311, 312, 313, 314 as the positive terminals. The contact pads 410 with the shape of a circular plate can squarely rest on top of the skull at the acupoints. Each contact pad 410 can be coupled to one signal, so the contact pad 410 is electrically connected to either the PWM generator 740 for coupling the pulse stimulation signal, or to the low reference voltage.

In the second embodiment, each individual contact of the plurality of contacts 300 comprises a spring 401 and a contact pad 410, wherein the contact pad 410 comprises a first zone 431 and a second zone 432. The first zone 431 and the second zone 432 are separated by an insulating material 433. The first zone 431 is electrically connected to the PWM generator 740 for coupling the pulse stimulation signal and the second zone is electrically connected to the low reference voltage. The second embodiment is developed for use in the second group of contacts 330 and the third group of contacts 320, which is a single contact point positioned for contacting the Shenting (GV-24) 12 as well as the Fengchi (GB-20) 13 acupoints.

In the third embodiment, each individual contact of the plurality of contacts 300 comprises a spring 401 and a contact pad 420 having plural pin electrodes 421. The plural pin electrodes 421 allow the contact pad 420 to penetrate through the hair for contacting the skin of the head 20. The third embodiment is developed for patients with more hair, and is preferably used in the first group of contacts 310, with the first contact pad 315 as the negative terminal, and four adjacent contact pads 311, 312, 313, 314 as the positive terminals. The spring 401 is arranged to press the plural pin electrodes 421 through the hair of the patient against the head 20 at the acupoints. Therefore, the pin electrodes 421 can ensure a better contact with the skin under the hair canopy. Another benefit bought by the third embodiment is the possibility of coupling more than one signal with one contact. As illustrated, at least one pin electrode 421A of the plural pin electrodes 421 is electrically connected to the PWM generator 740 for coupling the pulse stimulation signal, and at least one other pin electrode 421B of the plural pin electrodes 421 are electrically connected to the low reference voltage.

The plurality of contact pads 300 should be capable of coupling electric signals to the patient. Therefore, the plurality of contact pads 300 is made of a low resistance conductive material, such as copper, aluminum, gold, nickel, other metallic material, or any combination thereof.

Another aspect of the present disclosure provides one or more thermal pads 340 for applying thermal modalities to the acupoints. In the illustrated embodiment, one thermal pad is provided on the upper frame 220 near the first group of contacts 310. Two thermal pads are also provided on the lower frame 230 near the second group of contacts 330. It is apparent that one further thermal pad (not shown) may be provided near the third group of contacts 320 without departing from the scope and spirit of the present disclosure.

The one or more thermal pads 340 are electricity generated heating pads configured to deliver heat to at least one of the acupoints of the patient and areas proximate to the at least one of the acupoints. As shown in FIG. 6, each of the one or more thermal pads 340 comprises electrical cables 342 and a winding 341 of a thermally conductive material for delivering a temperature ranging between 36° C. and 40° C. The winding 341 may have a symmetrical routing pattern, a spiral routing pattern, or other patterns. The purpose of the one or more thermal pads 340 is to deliver thermal energy to the at least one of the acupoints and the areas proximate to the at least one of the acupoints with a temperature ranging between 36° C. and 40° C. The rise in temperature above the normal body temperature can improve blood circulation in the head, which can improve the cognitive functions and memory of the patient. Each thermal pad 340 is sized and positioned to conform to the locations of the acupoints to be stimulated. In certain embodiments, the thermal pads 340 are provided on the plurality of contacts 300.

Figure 7:
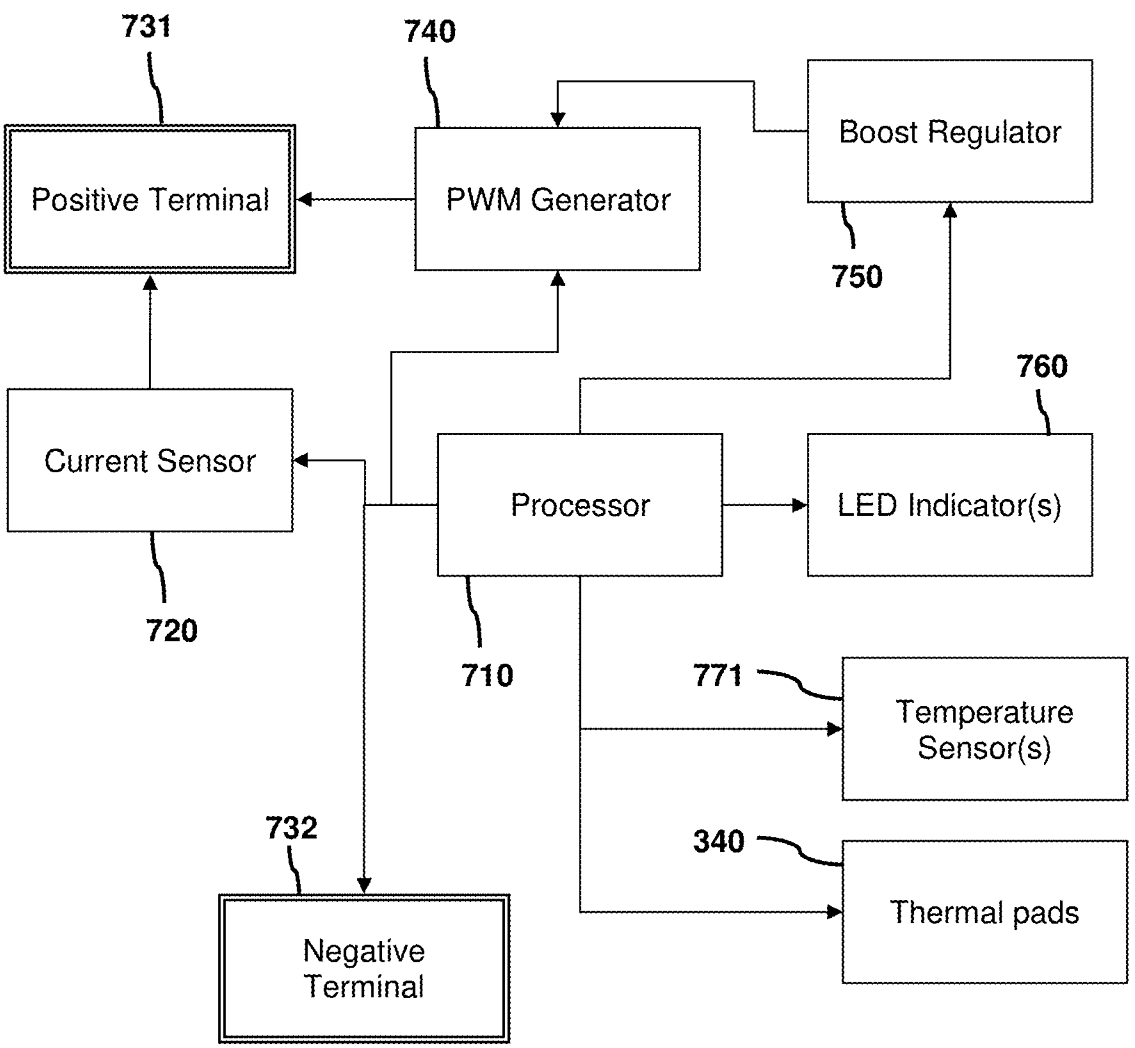
FIG. 7 is a system block diagram of a TENS device adapted to stimulate acupoints of a patient for treating or preventing dementia in accordance with certain embodiments of the present disclosure.

Referring to FIG. 7, an exemplary system block diagram of the TENS device 100 is illustrated. The TENS device 100 further comprises a processor 710, a PWM generator 740, a boost regulator 750, one or more temperature sensors 771, a current sensor 720, and one or more light-emitting diode (LED) indicators 760.

In particular, the one or more temperature sensors 760 obtain temperature readings of areas proximate to the one or more thermal pads 340 to ensure that the temperature is ranged between 36° C. and 40° C. The PWM generator 740 is configured to generate a pulse stimulation signal at a positive terminal 731, and the negative terminal 732 completes the circuit through the patient by connecting to the GND or a low reference voltage. The current sensor 720 is provided for detecting an electric current flowing through the patient via the plurality of contacts 300. The current sensor 720 is a high-precision current sensor that can detect ultra-low current in the μA range. The processor 710 is configured to monitor and adjust the one or more thermal pads 340 and the PWM generator 740 continuously based on the temperature detected by the one or more temperature sensors 771 and the electric current detected by the current sensor 720. Preferably, the processor 710 is a microcontroller embedded in the control box 210. In other alternative embodiments, the processor 710 may be a discrete control device, a computation system implemented by a portable device, a personal computer, a cloud-based server, or other electronic devices capable of performing computation. The control box 210 is also provided with one or more LED indicators 760 for indicating the status of the TENS device 100, which can alert the caregiver when there is an abnormal operation. The boost regulator 750 is configured to generate reference voltages for the PWM generator 740 and other electronic components. In certain embodiments, the boost regulator 750 generates voltage ranges from 5V to 120V.

Figure 8:
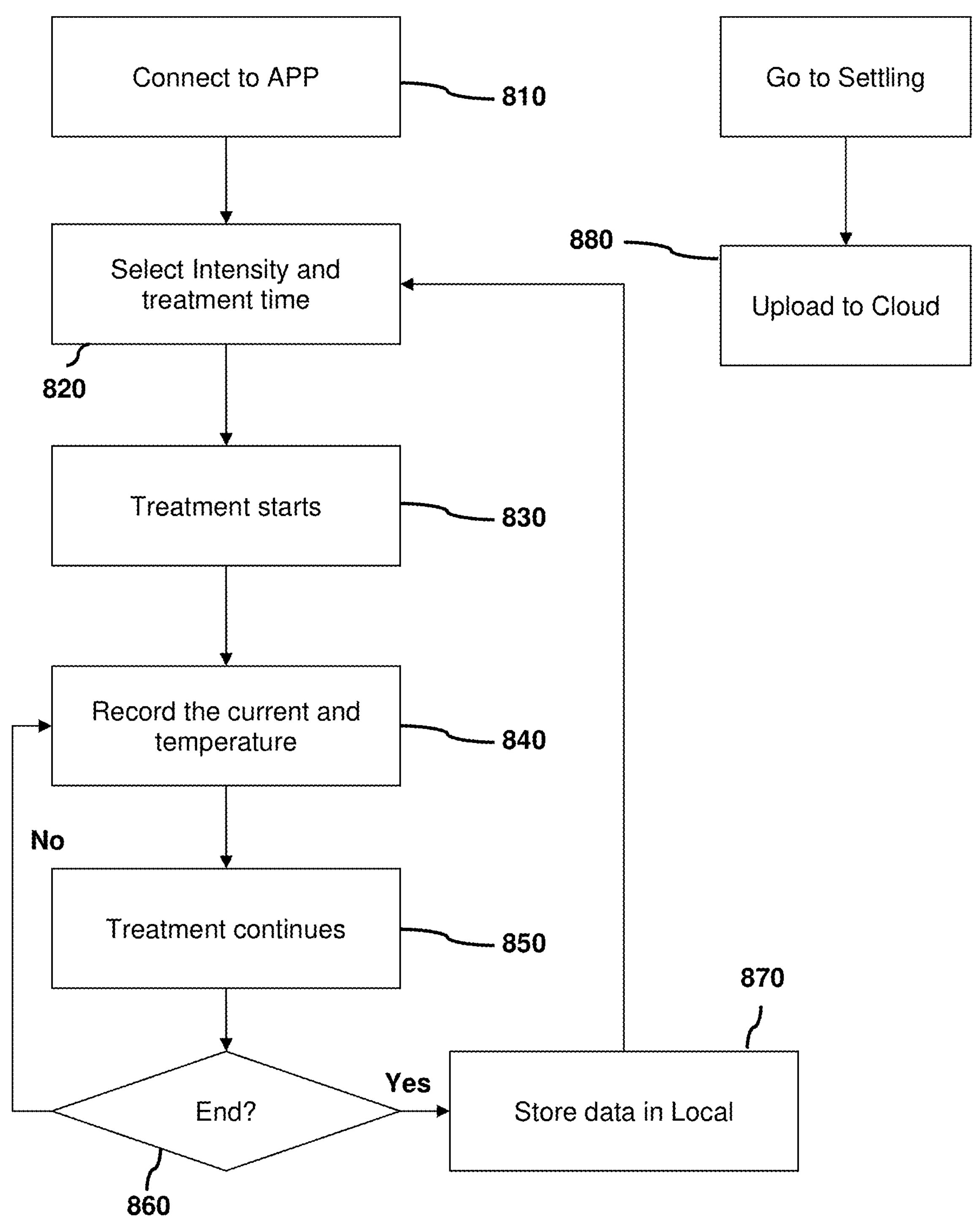
FIG. 8 is a flowchart illustrating the method of stimulating acupoints of a patient for treating or preventing dementia in accordance with certain embodiments of the present disclosure.

FIG. 8 is a flowchart illustrating the method of stimulating acupoints of a patient using the TENS device 100 of the present disclosure for treating or preventing dementia. The caregiver can first properly place and position the TENS device 100 on the head 20 of the patient, such that the plurality of contacts 300 and the one or more thermal pads 340 arranged on the inner surface of the TENS device 100 can properly contact the acupoints on the head 20. When it is done, the TENS device 100 should be connected to the app 810 for control and data logging by wireless communication. The caregiver uses the app to select the intensity and treatment time 820. Then the treatment is started 830. The electric current and temperature readings of areas proximate to the thermal pads 340 are recorded 840 while the treatment continues 850. The processor 710 regularly determines whether the operation treatment should continue 860, and when the treatment is completed, the electric current and temperature readings recorded are stored locally in the memory 870 of the TENS device 100. Output of these data can be seen in the Apps from the controlling device or computer system. In certain embodiments, these data are presented as diagrams and graphs. The caregiver can any-time upload the stored data to a cloud system 880, which can be accessed by the medical practitioners or therapists.

This illustrates ultra-low constant current head-mount TENS device with thermal modalities in accordance with the present disclosure. It will be apparent that variants of the above-disclosed and other features and functions, or alternatives thereof, may be combined into many other different configurations and systems. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

Figure 9A:
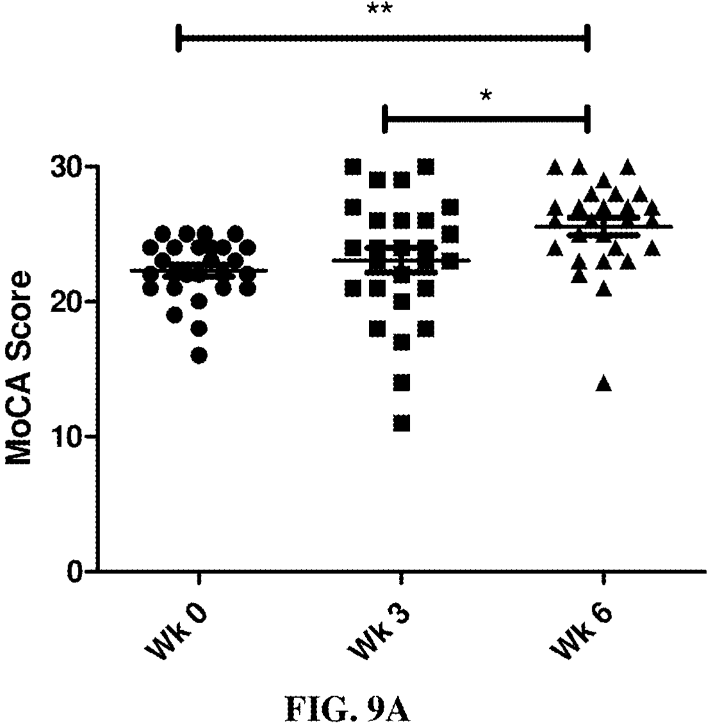
FIG. 9A shows TENS hat treatment increases Montreal Cognitive Assessment (MoCA) scores for patients with mild cognitive impairment (MCI) for a period of six weeks in accordance with certain embodiments of the present disclosure.
Figure 9B:
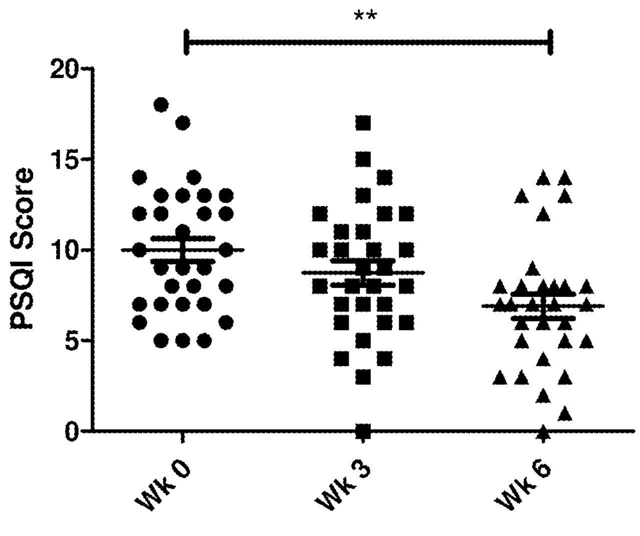
FIG. 9B shows TENS hat treatment reduces Pittsburgh Sleep Quality Index (PSQI) scores for patients with MCI for a period of six weeks in accordance with certain embodiments of the present disclosure.

Referring to FIGS. 9A and 9B, the clinical efficacy of the TENS devices as described above in accordance with one or more embodiments has been demonstrated. Sleeping disturbance (insomnia) is a common issue associated with dementia and tends to become more severe as dementia progresses. In the present demonstration, the efficacy of a TENS hat on the sleeping quality of patients with MCI is studied as an example, where the TENS hat is a specific implementation of various TENS devices as described above with reference to one or more figures.

In this exemplified study, fifty-eight patients (average age: 72.5 years old; Male: 9; Female: 49) with mild cognitive impairment (MCI) (MoCA score<26) are recruited and treated with the TENS hat for a period of 6 weeks (30 min/session; 3 times/week). All the patients are Chinese background. An independent investigator evaluates the effects of TENS on cognitive function and sleeping quality respectively on day 0 (baseline), the third week (also called week 3, 3-week, or Wk 3) (mid-term), and the sixth week (also called week 6, 6-week, or Wk 6) (end-point) of the trial period. Montreal Cognitive Assessment (MoCA) is used to evaluate the cognitive functions of the patients. MoCA is a highly sensitive instrument for detection of MCI. It assesses multiple cognitive domains, including attention and concentration, executive functions, memory, language, visuoconstructional skills, conceptual thinking, calculations, and orientation. The scores range between 0 and 30, and a subject with a score of 26 or over is considered normal. A Hong Kong version of MoCA (HK-MoCA) is used in this study. Assessment of the sleeping quality is evaluated using Pittsburgh Sleep Quality Index (PSQI) tests. PSQI is a self-rated questionnaire which assesses sleep quality and disturbances over a 1-month time interval. The scores range from 0 to 21, and a subject with a score>5 is considered as having significant sleep disturbance. All statistical analyses are performed using Prism GraphPad software. Differences are examined using one-way Analysis of Variance (ANOVA) test. A difference with a P value<0.05 is considered as statistically significant. Data are expressed in mean±standard deviation (S.D.).

As shown in FIGS. 9A, the average MoCA score before the treatment is 22.30±2.33. The MoCA scores improves to 23.07±4.68 and 25.56±3.37 after 3-week and 6-week (Baseline vs Week 6, P<0.01) of treatment, respectively. This shows the TENS has improved cognitive functions of the patients. Referring to FIGS. 9B, the TENS hat further shows a favorable response in the majority of patients with sleep disturbance. The results show that the TENS hat significantly reduces the PSQI score from 10.0±3.504 to 8.7±3.732 after 3-week of treatment and further to 6.9±3.652 after 6-week (Baseline vs Week 6, P<0.01) of treatment. These improvements are statistically significant by ANOVA analysis. In conclusion, the results show that 6-week TENS hat treatment significantly improves cognitive functions and sleeping quality in patients with MCI.

LIST OF REFERENCES

There follows a list of references that are occasionally cited in the specification. Each of the disclosures of these references is incorporated by reference herein in its entirety.

[1] Salzmann E. et al., Importance of the hippocampus and parahippocampus with reference to normal and disordered memory function, Fortschr Neurol Psychiatr 1992; 60:163-76.

[2] Swaab D F, et al., Brain aging and Alzheimer's disease; use it or lose it, Prog Brain Res 2002; 138:343-73.

[3] Burstein R, et al., Retrograde labeling of neurons in spinal cord that project directly to nucleus accumbens or the septal nuclei in the rat, Brain Res 1989; 497:149-54.

[4] Giesler Jr G J, et al., Direct spinal pathways to the limbic system for nociceptive information, Trends Neurosci 1994; 17:244-50.

[5] Cape E G, et al., Differential modulation of high-frequency gamma-electroencephalogram activity and sleep-wake state by noradrenaline and serotonin micro-injections into the region of cholinergic basalis neurons, J Neurosci 1998; 18:2653-66.

[6] Fort P, et al., Noradrenergic modulation of cholinergic nucleus basalis neurons demonstrated by in vitro pharmacological and immunohistochemical evidence in the guinea-pig brain, Eur J Neurosci 1995; 7:1502.

[7] Kalen P, et al., Projections from the medial septum and diagonal band of Broca to the dorsal and central superior raphe nuclei: a non-cholinergic pathway, Exp Brain Res 1989; 75:401-16.

[8] Kayama Y, et al., Brainstem Neural Mechanisms of Sleep and Wakefulness, Eur Urol. 1998; 33 Suppl 3:12-5.

[9] Waterhouse B D, et al., The distribution of neocortical projection neurons in the locus coeruleus, J Comp Neurol. 1983; 217:418-431.

[10] Swaab D F, et al., Therapeutic strategies for Alzheimer disease: focus on neuronal reactivation of metabolically impaired neurons, Alzheimer Dis Assoc Disord 2003; 17(Suppl 4): S114-22.

[11] Scherder E J A, et al., Influence of transcutaneous electrical nerve stimulation on memory in patients with dementia of the Alzheimer type, J Clin Exp Neuropsychol 1992; 14:951-960.

[12] Scherder E J A, et al., Effects of short-term transcutaneous electrical nerve stimulation on memory and affective behavior in patients with probable Alzheimer's disease, Behav Brain Res 1995; 67:211-219.

[13] Scherder E J A, et al., Effects of a follow-up treatment of short-term transcutaneous electrical nerve stimulation on memory and affective behavior in a patient with probable Alzheimer's disease, Behav Neurol 1996; 9:33-35.

[14] Scherder E J, et al., Effects of transcutaneous electrical nerve stimulation on memory and behavior in Alzheimer's disease may be stage-dependent, Biol Psychiatry 1999; 45: 743-9.

[15] Luijpen M W, et al., Effects of Transcutaneous Electrical Nerve Stimulation (TENS) on memory in elderly with mild cognitive impairment, Behavioral Brain Research 2005; 158: 349-357.

[16] Van Dijk K R A, et al., Effects of Transcutaneous Electrical Nerve Stimulation (TENS) on non-pain related cognitive and behavioral functioning, Reviews in the Neurosciences 2002; 13: 257-270.

[17] Zhang H, et al., Clinical observation on effect of scalp electroacupuncture for mild cognitive impairment, Tradit Chin Med 2013, 33(1):46-50.

[18] Dowswell T, et al., Transcutaneous electrical nerve stimulation (TENS) for pain relief in labour, Cochrane Database Syst Rev. 2009, 2: CD007214.

[19] Schoenen J, et al., Migraine prevention with a supraorbital transcutaneous stimulator: a randomized controlled trial, Neurology 2013, 80(8):697-704

What is claimed is:

1. A head-mount transcutaneous electrical nerve stimulation (TENS) device adapted to stimulate acupoints of a user transcutaneously when being worn on the head of the user, comprising:

one or more frames arranged to have a contour matching an anatomical shape of the head, wherein the one or more frames comprises an upper frame at least partially covering a frontal region and a parietal region of the head, and a lower frame at least partially covering an occipital region of the head;

a plurality of contacts arranged on an inner surface of the one or more frames for contacting the acupoints on the head;

a pulse width modulation (PWM) generator configured to generate a pulse stimulation signal having an ultra-low current between 1 μA and 8 μA and couple the pulse stimulation signal to the plurality of contacts for stimulating the acupoints; and one or more thermal pads arranged on the inner surface of the one or more frames for applying thermal treatment to at least one of the acupoints, wherein the head-mount TENS device further comprises a single control box that is placed on top of the upper frame and houses the PWM generator therein, the control box comprising an electric circuit board and associated accessories for controlling the plurality of contacts, the control box connecting to the upper frame and lower frame via electric wirings.

2. The head-mount TENS device of claim 1, wherein the plurality of contacts comprises a first group of contacts configured for contacting Baihui (GV-20) and Sishencong (EX-HN1) acupoints of the user.

3. The head-mount TENS device of claim 1, wherein the plurality of contacts comprises a second group of contacts configured for contacting Fengchi (GB-20) acupoints of the user.

4. The head-mount TENS device of claim 1, wherein the plurality of contacts comprises a third contact configured for contacting Shenting (GV-24) acupoint of the user.

5. The head-mount TENS device of claim 1, wherein the plurality of contacts comprises:

a first group of contacts configured for contacting Baihui (GV-20) and Sishencong (EX-HN1) acupoints of the user;

a second group of contacts configured for contacting Fengchi (GB-20) acupoints of the user; and a third contact configured for contacting Shenting (GV-24) acupoint of the user.

6. The head-mount TENS device of claim 2, wherein the first group of contacts comprises a first contact pad positioned for contacting the Baihui (GV-20) acupoints, and four adjacent contact pads positioned around the first contact pad for contacting the Sishencong (EX-HN1) acupoints.

7. The head-mount TENS device of claim 1, wherein each individual contact of the plurality of contacts has a resilient structure made of a metallic conductive material.

8. The head-mount TENS device of claim 7, wherein each individual contact comprises a spring and a contact pad, wherein the spring is arranged to press the contact pad against the head at the acupoints.

9. The head-mount TENS device of claim 8, wherein the contact pad is a circular plate electrically connected to the PWM generator for coupling the pulse stimulation signal or to a ground (GND) voltage potential.

10. The head-mount TENS device of claim 8, wherein the contact pad comprises a first zone and a second zone, wherein:

the first zone and the second zone are separated by an insulating material; and the first zone is electrically connected to the PWM generator for coupling the pulse stimulation signal and the second zone is electrically connected to the ground (GND) voltage potential.

11. The head-mount TENS device of claim 7, wherein the individual contact comprises a spring and a contact pad having plural pin electrodes, wherein the spring is arranged to press the plural pin electrodes through the hair of the user against the head at the acupoints.

12. The head-mount TENS device of claim 11, wherein at least one pin electrode of the plural pin electrodes is electrically connected to the PWM generator for coupling the pulse stimulation signal, and at least one other pin electrode of the plural pin electrodes is electrically connected to a ground (GND) voltage potential.

13. The head-mount TENS device of claim 1, wherein the pulse stimulation signal is a square wave with a pulse frequency between 96 Hz and 100 Hz.

14. The head-mount TENS device of claim 1, wherein the one or more thermal pads are configured to deliver heat to the at least one of the acupoints of the user and areas proximate to the at least one of the acupoints.

15. The head-mount TENS device of claim 14, wherein each of the one or more thermal pads comprises a winding of a thermally conductive material for delivering thermal energy to the at least one of the acupoints and the areas proximate to the at least one of the acupoints with a temperature ranging between 36° C. and 40° C.

16. The head-mount TENS device of claim 1, wherein the upper frame and the lower frame are adjustably connected together using connection means.

17. The head-mount TENS device of claim 16, wherein the connection means comprises straps or belts for providing a flexibility to adjust the contour for matching the anatomical shape of the head.

18. The head-mount TENS device of claim 1 further comprising fastening means for applying a tension on the upper frame and the lower frame toward the acupoints.

19. The head-mount TENS device of claim 18, wherein the fastening means comprises a chin strap fastened around the user's chin and two transverse straps extending from the upper frame to the lower frame, wherein the chin strap and each of the transverse straps are connected to form a Y-shaped configuration around an otic region for securing the head-mount TENS device in position on the head.

20. The head-mount TENS device of claim 1, further comprising:

one or more temperature sensors for obtaining temperature readings of areas proximate to the one or more thermal pads;

a current sensor for detecting an electric current flowing through the user via the plurality of contacts; and a processor configured to monitor and adjust the one or more thermal pads and the PWM generator continuously based on the temperature detected by the one or more temperature sensors and the electric current detected by the current sensor.

21. A method of stimulating selected acupoints of a user, comprising the steps of:

positioning the head-mount TENS device of claim 1 on the head of the user;

generating, by the PWM generator of the head-mount TENS device, a pulse stimulation signal having an ultra-low current between 1 μA and 8 μA;

coupling the pulse stimulation signal to the plurality of contacts for stimulating the acupoints transcutaneously; and enabling the one or more thermal pads for applying thermal treatment to the acupoints.

22. The method of claim 21, wherein the plurality of contacts comprises:

a first group of contacts configured for contacting Baihui (GV-20) and Sishencong (EX-HN1) acupoints of the user;

a second group of contacts configured for contacting Fengchi (GB-20) acupoints of the user; and a third contact configured for contacting Shenting (GV-24) acupoint of the user.

23. The method of claim 22, wherein the first group of contacts comprises a first contact pad positioned for contacting the Baihui (GV-20) acupoints, and four adjacent contact pads positioned around the first contact pad for contacting the Sishencong (EX-HN1) acupoints.

24. The method of claim 21 further comprising the steps of:

recording an electric current flowing through the user and temperature readings of areas proximate to the one or more thermal pads;

storing the electric current and the temperature readings locally in a memory of the TENS device; and uploading the electric current and the temperature readings to a cloud system for medical practitioners or therapists to access.

* * * * *